United States Patent [19]

Haynes

[11] Patent Number: 5,246,707
[45] Date of Patent: * Sep. 21, 1993

[54] SUSTAINED RELEASE DELIVERY OF WATER-SOLUBLE BIO-MOLECULES AND DRUGS USING PHOSPHOLIPID-COATED MICROCRYSTALS, MICRODROPLETS AND HIGH-CONCENTRATION LIPOSOMES

[76] Inventor: Duncan H. Haynes, 4051 Barbarossa Ave., Miami, Fla. 33133

[*] Notice: The portion of the term of this patent subsequent to Feb. 25, 2009 has been disclaimed.

[21] Appl. No.: 800,520

[22] Filed: Dec. 3, 1991

Related U.S. Application Data

[63] Continuation-in-part of Ser. No. 514,012, Apr. 26, 1990, Pat. No. 5,091,188.

[51] Int. Cl.$^5$ .................. A61K 37/22; A61K 9/127
[52] U.S. Cl. .................... 424/450; 424/88; 424/89; 424/90; 424/92; 424/405; 424/408; 424/409; 424/420
[58] Field of Search ............. 424/450, 420, 405, 408, 424/409, 88, 92, 89, 90

[56] References Cited

U.S. PATENT DOCUMENTS

| | | | |
|---|---|---|---|
| 4,053,585 | 10/1977 | Allison et al. | 424/92 |
| 4,078,052 | 3/1978 | Papahadjopoulos et al. | 424/36 |
| 4,133,874 | 1/1979 | Miller et al. | 424/38 |
| 4,325,871 | 11/1980 | Papahadjopoulos et al. | 424/19 |
| 4,331,654 | 5/1982 | Morris | 424/38 |
| 4,411,894 | 10/1983 | Schrank | 424/199 |
| 4,515,736 | 5/1985 | Deamer | 264/4.3 |
| 4,610,868 | 9/1986 | Fountain | 424/1.1 |
| 4,622,219 | 11/1986 | Haynes | 424/38 |
| 4,687,762 | 8/1987 | Fukushima et al. | 514/34 |
| 4,752,442 | 6/1988 | Asada et al. | 420/507 |
| 4,756,910 | 7/1988 | Yagi et al. | 424/450 |
| 4,761,288 | 8/1988 | Mezei | 424/450 |
| 4,762,720 | 8/1988 | Jizomoto | 424/450 |
| 4,776,991 | 10/1988 | Farmer et al. | 264/4.3 |
| 4,803,070 | 2/1989 | Cantrell et al. | 424/92 |
| 4,806,350 | 2/1989 | Gerber | 424/88 |
| 4,806,352 | 2/1989 | Cantrell | 424/92 |
| 4,826,687 | 5/1989 | Nerome et al. | 424/450 |
| 5,030,453 | 7/1991 | Lenk et al. | 424/450 |

FOREIGN PATENT DOCUMENTS

| | | |
|---|---|---|
| 0272091 | 6/1988 | European Pat. Off. . |
| WO85/00011 | 1/1985 | PCT Int'l Appl. . |
| 2046094A | 11/1980 | United Kingdom . |
| WO87/04592 | 8/1987 | World Int. Prop. O. . |
| WO91/04011 | 4/1991 | World Int. Prop. O. . |

*Primary Examiner*—Thurman K. Page
*Assistant Examiner*—G. S. Kishore
*Attorney, Agent, or Firm*—Nixon & Vanderhye

[57] ABSTRACT

The novel uses of the phospholipid-coated microcrystal in the delivery of water-soluble biomolecules such as polypeptides and proteins. The proteins are rendered insoluble by complexation and the resulting material forms the solid core of the phospholipid-coated particle. Alternatively, the proteins, bio-molecules or drugs can be entrapped in water-soluble form between the membranous layers of the coated microcrystal. All types of phospholipid microcrystals can incorporate 5 nm to 10 um diameter iron oxide particles to allow for manipulation by magnetic fields. Water-soluble bio-molecules including proteins, peptides, and drugs can be entrapped and retained with long shelf life in liposomes at high concentrations, provided that the phospholipid concentration is greater than 10% (w/v) such that greater than 50% of the system volume is enclosed within phospholipid membranes. Both the phospholipid-coated microcrystal and the phospholipid-coated microdroplet can be used as vaccine adjuvants.

11 Claims, No Drawings

SUSTAINED RELEASE DELIVERY OF WATER-SOLUBLE BIO-MOLECULES AND DRUGS USING PHOSPHOLIPID-COATED MICROCRYSTALS, MICRODROPLETS AND HIGH-CONCENTRATION LIPOSOMES

This is a continuation in part of Ser. No. 514,012 filed Apr. 26, 1990, now U.S. Pat. No. 5,091,188.

This invention relates to additional pharmaceutical uses of the phosphilipid-coated microdroplet (Haynes, U.S. Pat. No. 4,622,219; Haynes, U.S. Pat. No. 4,725,442) now U.S. Pat. No. 5,091,188. The above-cited documents described the utility of these compositions of matter in the delivery of water insoluble drugs. Both the microdroplet and the microcrystal are able to incorporate water-insoluble drugs at high payload. In the microdroplet, the oil phase is itself a drug or dissolved a drug. In the microcrystal, the core is pure drug in crystalline or solid form. In both cases, the phospholipid coating was shown to both render the microdroplets or microcrystals stable in aqueous suspension and to provide tissue-compatible, making the preparations non-irritating.

The present Specification shows that the phospholipid-coated microcrystal is also a useful means of delivery of water-soluble biological molecules. The biomolecule can either be rendered insoluble by complexation or can be entrapped between the phospholipid membranes comprising the lipid coating of the microcrystal. Incorporation of magnetized iron oxide particles allows for external manipulation.

The teachings and working examples of the previous Specification for the phospholipid-coated microcrystal showed that when the phospholipid concentration is in the 10–20% (w/v) range, the majority of the aqueous volume is enclosed within or between membrane layers. The present Specification shows how this property can be useful means of sustained-release delivery of water-soluble molecules and drugs by using concentrated liposomes: Syringability, injectability, greater than 50% capture of the carried/entrapped molecule and extremely long shelf life insensitive to "leakage", can all be achieved at phospholipid concentrations greater than 10% (w/v).

The present Specification will also show that the phospholipid-coated microdroplet can be used to increase the residence time and antigenicity of water-soluble molecules, membrane fragments and particles in solid living tissues when it is coinjected with the above. The microcrystal can also be used as a vaccine adjuvant.

BACKGROUND OF INVENTION

Both the phospholipid-coated microdroplet and the phospholipid-coated microcrystal depend on the membrane-forming and amphipathic properties of phospholipids to maintain their structure. As described in the previous Specification (Haynes, U.S. application Ser. No. 07/514,012 now U.S. Pat. No. 5,091,188), fatty acids and detergents are also amphipathic, but do not form membranes. Phospholipids are the major building block of biological membranes, and are very tissue compatible. An important and abundant example is lecithin (phosphatidylcholine). In the presence of excess water, phospholipids form membranes of bimolecular thickness. The polar head groups are oriented to the water; the fatty acyl chains form a palisade structure, with their ends abutting in the center of the membrane.

Liposomes, aqueous core vesicles formed from membrane-forming phospholipids such as lecithin, were first described by Bangham, Standish & Watkins (in J. Mol. Biol. 13:238, 1965). Liposomes produced by homogenization are multi-lamellar, with concentric bilayer membranes. Liposomes produced by sonication are small and unilamellar phospholipid vesicles as described by Haung (in Biochem. 8:344, 1969). Liposomes have the ability to entrap polar and highly-charged molecules in their aqueous interiors. Publications describing the use of liposomes to entrap and deliver water-soluble drugs appeared in the early and mid-1970's (cf. Gregoriadis: "The Carrier Potential of Liposomes in Biology and Medicine", New. England Journal of Medicine 295:704–710, 1976). A large number of patents have been granted for entrapment of water-soluble drugs and proteins (Papahadjopoulos, U.S. Pat. No. 4,078,052, 1978; Schneider, U.S. Pat. No. 4,089,801, 1978; Miller & Djordjevich, U.S. Pat. No. 4,133,874, 1979; Papahadjopoulos et al., U.S. Pat. No. 4,235,871, 1980; Weber et al., U.S. Pat. No. 4,38,052, 1984; Deamer, U.S. Pat. No. 4,515,736, 1985; Jizomoto, U.S. Pat. No. 4,762,720, 1988; Farmer & Beissinger, U.S. Pat. No. 4,776,991, 1988; Yagi et al., U.S. Pat. No. 4,756,910, 1988; Lenk et al., U.S. Pat. No. 5,030,453 are a small fraction of the available examples). However, most of these liposome inventions rely on complicated methods of preparation, including dissolution in organic solvents and evaporation, treatment with detergents and the like. Furthermore, the intra-vesicular space as described in these publications is always less than 10% of the total aqueous space. Thus the "stability of the entrapment" is a serious consideration since slow permeation of the entrapped molecules while the preparation is on the shelf will result in 90% of the molecules eventually being outside of the liposomes, with loss of the intended benefit of the encapsulation.

In the course of working with the phospholipid-coated microcrystal system, which incorporates phospholipid up to 20% (w/v), it became apparent to me that injectable, pharmaceutically-acceptable liposome preparations encapsulating over 50% of a water-soluble drug can be made by the simple methods of homogenization, sonication or high shear. At this concentration the stability of entrapment during storage is not an issue since the probability of molecules diffusing in is equal to the probability of molecules diffusing out.

In the present invention I propose the incorporation of particles of iron oxide in the phospholipid-coated microcrystal. The use of iron oxide in pharmaceutical systems has already been described. Widder and Senyei (U.S. Pat. No. 4,345,588, 1982) described the IV injection of albumin microspheres consisting of drug, serum albumin and $Fe_3O_4$ powder in a ratio of 10:125:36. The albumin is crosslinked by formaldehyde. Particle diameter was 10 um. The phospholipid-coated microcrystal described by me previously (Haynes, U.S. application Ser. No. 07/514,012 now U.S. Pat. No. 5,091,188) does not rely on crosslinked albumin. Morris (U.S. Pat. No. 4,331,654, 1982) described a lyophilized preparation of <3 um diameter magnetically-localizable microspheres consisting of a core of magnetite ($Fe_3O_4$) coated with a solidified mixture of fatty acid and non-ionic detergent, and containing lecithin as a minor constituent. The phospholipid-coated microcrystal described by me previously (Haynes, U.S. application Ser. No. 07/514,012 now U.S. Pat. No. 5,091,188) does not rely on detergent to suspend the particles.

In this specification I also describe the use of the phospholipid-coated microcrystal and phospholipid-coated microdroplet as vaccine adjuvants. Much use has been made of phospholipids and oils in adjuvant systems, but no published system fits the description of the phospholipid-coated microcrystal or microdroplet. There is a considerable amount of published work on the use of liposomes as adjuvants (Allison & Gregoriadis, U.S. Pat. No. 4,053,585, 1977; Nerome et al., U.S. Pat. No. 4,826,687, 1989) and detergent-solublized oils as adjuvants (Gerber, U.S. Pat. No. 4,806,350, 1989). In the cases where phospholipids and oils have been used together, the systems contained detergents or contained high concentrations of ethylene glycol, propylene glycol or the like (Cantrell, U.S. Pat. No. 4,806,352, 1989; Cantrell & Rudbach, U.S. Pat. No. 4,803,070, 1989).

DESCRIPTION OF THE INVENTION

My invention provides compositions and procedures for sustained release delivery of water-soluble drugs and biomolecules by incorporation into phospholipid-coated microcrystals. Water-soluble bio-molecules can either be rendered insoluble by complexation and incorporated into the solid cores of phospholipid-coated microcrystals, or they can be incorporated in water-soluble form by entrapment between the membrane layers. After injection the bio-molecule must traverse the membrane layers before it can escape to the tissue. In the former case it also must first dissociate from its insoluble complex. Both of these processes give rise to slow release, such that the injected tissue and the system as a whole experience lower but sustained concentrations. This can give rise to more useful therapeutic effects of the bio-molecule. The inter-membranous entrapment mechanism is also useful for drugs. On the other hand, when the bio-molecule is antigenic and the injection is intradermal, subcutaneous or intramuscular, the longer residence time obtained with the microcrystal administration can translate into an adjuvant effect. Coinjection of high concentrations of phospholipid-coated microdroplets also increase the residence time of injected molecules and antigenic membrane fragments and virus particles and increase antibody titer.

Definitions:

The biological molecule (bio-molecule) can be a peptide, a polypeptide, a protein, a complex carbohydrate, a glycoprotein, a lipoprotein, a glycolipid, a hormone, a biological response modifier, deoxyribonucleic acid (DNA), ribonucleic acid (RNA) or any other natural product or product of genetic engineering. Also contemplated are supramolecular aggregates of one or more type of bio-molecule as in bacterial membrane fragments and viral coat proteins, the major limitation being that the aggregates must have dimensions less than 10 um. The use of low molecular weight drugs of defined structure has already been described (Haynes, U.S. application Ser. No. 07/514,012 now U.S. Pat. No. 5,091,188). For ease of description in difficult passages, I will sometimes use the term microcrystal when a phospholipid-coated microcrystal or particle of amorphous solid of <10 um diameter or maximal dimension) is intended.

Methods of Production:

Production is accomplished by appropriate combination of the steps described in the following subsections. Methods for size reduction can be categorized as two types: Those involving low shear producing smaller particles and those creating high shear producing larger particles. Low shear methods include Waring Blender, "high" and propeller homogenization and rotating tube and plunger homogenizers. High shear methods include the French Pressure Cell or "French Press" (SLM Instruments, Urbana Ill.), sonication (Heat Systems Co., Melville, N.Y.) and Microfluidization ® (Microfluidics Corp., Newton Mass. 02164). The latter, which is described by Mayhew et al. in Biochim. Biophys Acta 775:169-174, 1984, is particularly well suited for commercial production.

Precipitation of Bio-Molecule

This step is necessary for preparations in which the bio-molecule comprises the solid core of the phospholipid-coated microcrystal. For a water-soluble bio-molecule to remain stable in the preparation it must be rendered insoluble. Often the substance is insoluble or takes the form of a paste at 20% (w/v) concentration. It is possible to facilitate precipitation by lowering the water activity by increasing the glucose or salt concentration to high values. My experience has shown that living tissues tolerate high tonicity in phospholipid-coated microcrystal preparations. High tonicity can also accelerate the release rate. If the bio-molecule remains soluble at very high concentration, it is often possible to effect precipitation by small changes in pH or ionic composition. Precipitation can also be accomplished by adding a cationic macromolecule to an anionic protein and vice versa. An example is protamine precipitation of heparin. Useful cationic proteins include polyarginine, polylysine, polyhistidine and many proteins with isoelectric points greater than 8. Useful anionic proteins are polyglutamic acid, polyaspartic acid and many proteins with isoelectric points less than 6. In addition a number of salts can affect solubility. These include: 2-naphthylenesulfonate (napsylate), gluconate, 1,1'methylene bis(2-hydroxy-3-naphthalene)-carboxylic acid (pamoate), tolylsulfonate (tosylate), methanesulfonate (mersylate), glucoheptanoate (gluceptate), bitartrate, succinate, acetate, or behenate (anionic form of waxy fatty acid). In choosing fatty acyl anions it is advisable to select species with either short chain lengths or very long chain lengths, such that the tendency of towards micellarization is minimized. In some cases substitution with bromide, iodide, phosphate or nitrate may be effective. Examples of cationic species include calcium, magnesium or their 1:1 fatty acid salts, and various amines, including dibenzylethylenediamine (benzathine), N,N' (dihydroabietyl)ethylene diamine (hydrabamine) or polymers such as polylysine. The choice of these counterions is made largely on an empirical basis, with stability of the derived crystals or solid forms and biological stability being important criteria. Scientific literature describing the method of purification of the protein can be useful in this regard. In the case where none of the above strategies works to precipitate the bio-molecule it will be possible to remove it from solution by precipitation with an equal weight mixture of cationic and anionic polypeptides, such as polyarginine and polyglutamic acid. With sufficient study of the in vitro behavior of the phospholipid-coated microcrystals made from a number of these systems, and with judicious choice of the most promising examples, the desired in vivo pharmacokinetics can be approximated.

Size Reduction and Primary Coating:

Two cases must be distinguished: (A) When the insolublized bio-molecule is to comprise the solid core of the phospholipid-coated microcrystal and (B) when the bio-molecule, in soluble form, is to be entrapped between the membrane lamellae, with another pharmacologically-acceptable solid material comprising the core. In either case the core material must be reduced to <10 um or submicron dimensions in an aqueous medium. This can be accomplished by sonication or other treatments involving high shear. Lecithin (or other membrane forming lipid), present during the sonication, is itself broken into highly reactive fragments with exposed hydrophobic surfaces. These fragments coat and envelop the submicron core material creating a primary coating. A requirement for this process is that the lecithin and core material be present together during the sonication or alternative high-energy dispersing process. The common aspect of all of these preparative methods is that the fatty acyl chains of the phospholipid must have direct access to the core material during the coating process. In Case B, the bio-molecule in water-soluble form is entrapped within the enveloping layers of the primary coating. It is possible to increase the thickness of the primary coating by adding additional phospholipid to the suspension after sonication or high shear, and by suspending this phospholipid by homogenization at low shear ("high speed homogenizers", propeller homogenizers, Waring blender, or rotating tube and plunger homogenizers).

In my invention, the amphipathic properties of the phospholipid satisfy both the hydrophilic properties of water and the hydrophobic properties of the surface of the core material. Also, the phospholipid membrane surface serves as a stationary barrier to reformation of macroscopic crystals or solids. A second useful property of the primary coating is modification of the rate of the dissolution process of the insolublized bio-molecule. Firstly, the coprecipitants are also entrapped within the primary coating and the bio-molecule will thus remain in insoluble form until these are released. Secondly, the bio-molecules in soluble form will remain entrapped until the membranes comprising the primary coating are broken or otherwise disrupted. Possible structural features of the phospholipidmicrocrystal interaction have been schematized previously (Haynes, U.S. application Ser. No. 07/514,012 now U.S. Pat. No. 5,091,188).

Secondary Coating: Peripheral Phospholipid

In addition to making use of lecithin and other membrane-forming lipids as a coating and enveloping material, my invention makes novel use of membrane-forming lipids as mechanical buffers, organizers of aqueous volume and retardants of recrystallization of the drug. This is achieved by excess phospholipid in the form of unilamellar and multi-lamellar phospholipid vesicles which form a secondary coating of the suspended microcrystal. Bio-molecules in soluble form will also be entrapped within these structures if present during the sonication or high-shear process. Unilamellar vesicles are formed as the main byproduct of the sonication and primary coating process. Their retention in the preparation was found to improve the long-term stability of the formulation. Also, performed multi-lamellar vesicles (made by homogenization) or uni-lamellar vesicles can be added to the preparation to improve its stability or pharmacokinetics. Preformed vesicles can be made in the presence of the bio-molecule to entrap it in the aqueous volume encompassed by their membranes. The secondary coating is loosely attached to the coated microcrystal. Peripheral vesicles associate with and dissociate continuously in the preparation. Previous experimentation (Haynes, U.S. application Ser. No. 07/514,012 now U.S. Pat. No.5,091,188) has shown that the secondary coating can be removed by repeated centrifugation and resuspension of the preparation.

Peripheral vesicles forming a secondary coating stabilize the preparation. While not wishing to be bound to any particular theory or mode of action, detailed consideration has suggested the following mechanisms:

They act as volume buffers interposed between the primary-coated microcrystals. The crystalline and microcrystalline drugs are often more dense than the phospholipid which is, in turn, more dense than water. Thus they will tend to settle under the influence of gravity and will experience greater long-range interactions (van der Waals attraction) than the other two constituents. The secondary coating increases the distance of closest approach of the microcrystalline drug cores, thereby decreasing the van der Waals attraction. It is probable that part of the driving force for the secondary coating is van der Waals attraction between the primary-coated microcrystal and the phospholipid vesicle. Phospholipids (notably lecithin) are ideal as the primary and secondary coating because they are strongly hydrated and engage in well-documented short-range repulsive interactions which make them very resistant to aggregation and fusion.

When peripheral phospholipid is present at 20% (w/v), the majority of the aqueous volume of the preparation is enclosed within phospholipid membranes. This serves as a topological barrier to recrystallization of the drug in a preparation during long-term storage. Reformed crystals can not be larger than the diameter of the vesicles or distance between the vesicles. Both distances can be kept small.

Enclosure of the major portion of the aqueous volume by membranous structures ensures a high degree of the bio-molecule during preparation, renders "leakage" during shelf-life inconsequential, and retards the release process after injection into a living tissue.

Choice of Pharmacologically-Acceptable Core Material

In Case B, in which the water-soluble bio-molecule or drug is to be entrapped in water-soluble form between the membrane layers, it is necessary to provide another material comprising the microcrystal (microparticle) core. This can be any pharmacologically-acceptable water-insoluble substance which should generally have a water solubility of <5 mg/ml at physiological pH (6.5-7.4). It can be selected from, but is not limited to, paraffin, tristearin, ethyl oleate, cetostearyl alcohol, cetyl alcohol, myristy alcohol, stearyl alcohol, petrolatum on biocompatible polymer. The core material can also be selected from water-insoluble drugs, including but not limited to oxytetracycline (antibiotic), phenylbutazone (anti-inflammatory), cyclosporin (immunosuppressant) or an immunostimulating drug. There are many cases in which simultaneous treatment with a drug and bio-molecule is desirable.

Physical characteristics of the microcrystal preparation:

Sonication or high-shear is most conveniently carried out with the the core material at concentrations of 5% (w/v) or less and the membrane-forming lipid at 5% or greater. It is also convenient to add further core material and to repeat the process. With this method of stepwise addition, final concentrations of 20% core material can be achieved. The sonication or high-shear process results in a syringable suspension of coated microcrystals of predominantly sub-micron dimensions, with the particles exhibiting Brownian motion. Over a period of 1-2 days the microcrystals settle creating a distinct zone in which the concentration of core material is 20-40% (w/v). The final concentration and volume are dependent on the choice of core material and upon the choice of peripheral phospholipid concentration. In most preparations the bottom zone is resuspendable with inversion to give a homogeneous and syringable suspension, even after a period of months. For preparations in which this was not the case, resuspendability was obtained by increasing the peripheral phospholipid concentration.

The slow sedimentation process can be used as a means of concentrating the preparation. Removal of the volume above the sedimentation zone after 1-2 days results in preparations in which the core material is at 20-40% (w/v). Long-term storage results in no further settling. The preparations remain homogeneous, syringable and pharmaceutically acceptable for many months. Microscopic examination of these preparations reveals distinct micron and sub-micron diameter particles of core material. The volume between these is almost completely filled with the primary enveloping layers and by phospholipid vesicles. The latter can be conveniently visualized by Nile Red staining. In this concentrated form, the microcrystals exhibit only restricted Brownian Motion. Under microscopic observation they are not observed to change position in relation to eachother. They vibrate or "dance in place" about their central position. This partial restriction of motion is probably an important factor in the long-term stability of the preparation.

Lyophilization

The microcrystal and liposome products can be put into dry form by lyophilization to yield a powder which can be later reconstituted. This is useful when the long-term chemical stability of the to-be-encapsulated drug or bio-molecule in an aqueous environment is poor. The product can also be put into a capsule or be compacted into a tablet for oral administration.

Method of Preparation of High Concentration Liposomes

Water-Soluble bio-molecules and drugs can be delivered by liposomes. My studies in optimization of the phospholipid-coated microcrystal have show that liposomes can be prepared at high concentration (>10% w/v, typically 20% w/v), such that >50% of the aqueous volume is enclosed by liposomal membranes. This constitutes a syringable, injectable pharmaceutical composition for water-soluble, membrane-impermeant pharmacologically-active molecules. Entrapment is accomplished by adding to an aqueous solution of bio-molecule or drug a sample of dry or prehydrated phospholipid to a final concentration of 10-20% (w/v) while subjecting to high-speed homogenization, sonication, or high shear (as described above for the microcrystal).

Preparation and Physical Characteristics of the Phospholipid Coated Microdroplet Preparation This information has been given previously (Haynes, U.S. Pat. No. 4,725,422, 1988). In use of the microdroplet to decrease the rate of migration of a bio-molecule from its site of injection in a solid living tissue, it is most desirable to make the former with a persistent oil (low water solubility and low volatility), with the oil concentration in the final product in the 10-20% (w/v) range. This is because occupation and blocking of the interstitial aqueous space of the target tissue is important to the mechanism of retardation of migration of the bio-molecule. Oils having this property include vitamin E, other oil-soluble vitamins, squalene, squalene, triglycerides, fluorocarbons, chlorocarbons, fluorochlorocarbons, volatile anesthetics, isopropyl myristate, benzyl benzoate and other water-insoluble esters, ethers, silicones, oleyl alcohol and other water-insoluble esters or mineral oil.

Modes of Administration of Microcrystal and Microdroplet Formulations:

As noted above, the primary utility of the coated microcrystal is its injectability. Applicable injection sites are any living tissue or body cavity. They include but not limited to intra-venous (IV), intra-arterial (IA), intra-muscular (IM), intra-dermal, sub-cutaneous (Sub-Q), intra-articular, cerebro-spinal, epidural, intra-costal, intra-peritoneal, intra-tumor, intra-bladder, intra-lesional, sub-conjunctival, etc. Of particular usefulness are IM and Sub-Q administration for obtaining sustained release "depot" action. In addition, the phospholipid coating and submicron size of the preparation may prove to have advantages for oral use, both as an aqueous suspension and as a lyophilized product. Membranous encapsulation should protect proteins from the action of digestive enzymes, and the coated surface and mass of the microcrystal may be conducive to trans-epithelial transport of the bio-molecule in intact form. Similarly, the aqueous suspension may show advantageous for topical application, and instillation into the eye or ear. The preparation can deliver drugs by the inhalation route, in the form of either an aqueous suspension or a lyophilized powder.

The above is also applicable to the administration of the bio-molecule entrapped in phospholipid vesicles at phospholipid concentrations greater than 10% (w/v).

For application of bio-molecules or biologicals in water-soluble form by admixing and coadministration with phospholipid-coated microdroplets, intradermal, Sub-Q and IM injection is the most indicated route.

Rate of release after administration:

The most important determinant of the rate of release of the drug is the choice of injection site. If the formulation is injected intravenously, the drug or bio-molecule will be released to the system as rapidly as it crosses the membrane barrier of the microcrystal or liposome. For water-soluble drugs and low molecular weight natural products this rate will be determined by its non-specific permeability. For high molecular weight bio-molecules the process will require breakage or disruption of the membrane. This process can be facilitated by making the preparation hypertonic. For cases of very effective entrapment, the whole particle will be removed from the blood by endo- or phagocytotic processes.

When the microcrystal and liposome formulations are injected at high volume into a solid tissue such as muscle skin, the net rate of release can be exceedingly slow. The particles generally remain in the initial elements of volume created by the injection. These are generally macroscopic and there is little flow or agitation. Release of the bio-molecule or drug occurs by the same mechanism as discussed for the intravenous case except that diffusion of the released molecule out of the injected volume is still slower due to the larger diffusion distances involved. In the extreme, the release process can require upwards of 14 days. For high and fixed volumes and drug concentrations, the rate of removal can be increased by incorporation of hypertonic glucose. For preparations with residence times of greater than 7 days, the rate of release is affected by granulocyte activity.

In the case of conjection of water-soluble biomolecules or drugs admixed with phospholipid-coated microdroplets, the molecules are essentially free in the interstitial space of the injected solid tissue. In this case the retardation of the rate of diffusion from the tissue is partially dependent on blockage of the interstitial space by the microdroplets.

Section of Water-Soluble Bio-Molecule or Drug to be Incorporated:

If the water-soluble bio-molecule is to comprise the solid core of the microcrystal, it must be possible to render it solid as described above. If the water-soluble bio-molecule or drug is to be entrapped between the membranes of the microcrystal or liposome then it must nor bind the membranes or disrupt them. It is desirable that the molecule have a half-time of 30 min. or longer for crossing a single phospholipid membrane, although some benefit can be gained for drugs with half-times of crossing as low as approx. 30 sec (e.g. IV infusion of cytotoxic drugs). It is desirable that the drug be chemically stable in a humid environment. Otherwise it may be necessary to produce lyophilized forms.

Selection of the Membrane-Forming Lipids for Coating:

The primary requirement is that the coating lipid be membrane-forming. This is satisfied by all lipids which, in the presence of excess water, make bilayer structures of the type is well-documented for phospholipid vesicles or lipsomes. This requirement is not satisfied by fatty acids, detergents, non-ionic surfactants (e.g. polyethylene glycol) or triglycerides (vegetable oils, tristearin, "fats"). A secondary requirement is that the lipid not have a proclivity for converting into micellar structures. The excludes phospholipids or short chain length (6 or less) or lyso-lecithin (containing a single fatty acyl chain). High stability of the coating material in membrane form is necessary to keep the drug material from rearranging into macroscopic crystals. This is one reason why non-ionic surfactants do not work well for my intended purpose.

Useful examples of membrane-forming lipids are given below:

CLASS A: Primary phospholipids (usable in pure form) include the following:

Lecithin (phosphatidyl choline)
Sphingomyelin
Synthetic zwitterionic phospholipids or phospholipid analogues To this class belong all phospholipids which spontaneously form membranes when water is added. These phospholipids can be used in pure form to produce coated-microcrystals. Of all the phospholipids, lecithin is the most useful example because of its high availability and low cost.

CLASS B: Phospholipids capable of calcium-dependant aggregation. These phospholipids include the following:

Phosphatidic acid
Phosphatidyl serine
Phosphatidyl inositol
Cardiolipin (disphosphatidyl glycerol)
Phosphatidyl glycerol These lipids carry a negative charge at neutral pH. Preferably these phospholipids can be mixed with lecithin to obtain negatively-charged surfaces which will give repulsion between particles. When introduced into a medium containing 2 mM calcium (such as blood or interstitial), membranes containing these phospholipids are expected to show elevated aggregation and higher reactivity with cell membranes. This can be useful in causing the injected microcrystals to aggregate within the tissue, giving slower release rates. The usefulness of this class is limited by the high cost of these phospholipids, relative to lecithin.

CLASS C: Phosphatidyl ethanolamine promotes aggregation in a calcium-independent manner. It can be used in the pure form to coat microcrystals at pH 9. When the pH is brought to 7, as upon injection into blood or tissue the membranes become reactive, causing the particles to aggregate and to attach to cell membranes. This can have the useful property of slowing the release rate.

CLASS D: Cholesterol and steroids. These can ont be used as a sole coating material: They do not form membranes in the pure state. They can be added to the lecithin or other coating material to change its surface activity, the "microviscosity" or distensibility of the coating. With a steroid hormone (estrogen, androgen, mineralo- or glucocorticoid), it is possible to influence the local tissue response to the microcrystals as well as influencing their physical disposition.

CLASS E: Semi-lipoidal molecules can be incorporated into the phospholipid or glycerol lipid membrane and change the surface activity of the microdroplet. Molecules included in this class are the following:

Stearylamine or other long-chained alkyl amines which can be primary, secondary, tertiary or quaternary substituted. These give the microcrystal coating a positive charge and make them more reactive with cell membranes. Benzalkonium chloride is an aromatic example which is particularly useful because it also functions as a preservative against microbiological growth in the preparation.

Fatty acids. These can be incorporated at low concentrations (<0.02 gm/gm phospholipid) to alter the phospholipid packing and reactivity.

CLASS F: Membrane-active agents, glycolipids and glycoproteins to modify surface properties. Examples of membrane-active agents include nystatin, amphotericin B and gramicidin which are surface-active antibiotics. These have been shown to bind to the surfaces of phospholipid membranes and change their permeability. Glycolipids or glycoproteins could be included as a means of modifying surface reactivity. Likewise, antibodies can be coupled to membrane constitutents to direct or retain the microcrystal association with targeted cells or tissues. (Glycolipids, glycoproteins, and anti-bodies are classified as "biologicals". They would have to be screened for pyrogenicity, antigenicity etc. before use, and the process of gaining regulatory approval for such formulations would be more complex.)

CLASS G: Mono-glycerides.

These are not phospholipids, but they have been shown capable of forming oriented monolayers and bilayers in the presence of decane (Benz et al. Biochim. Biophys. Acta 394:323–334, 1975). They may thus prove have some use in coating for microcrystals. Examples of these lipids include, but are not limited to, the following:

1-monopalmitoyl-(rac)-glycerol (Monopalmitin)
1-monocaprylol-(rac)-glycerol (Monocaprylin)
1-monooleoyl-(rac)-glycerol (C18:1, cis-9) (Monoolein)

1-monostearyl-(rac)-glycerol (Monostearin)

Commercially Available Membrane-Forming Lipids:

Several forms of lecithin are contemplated. As an example, egg lecithin (Pfanstiehl Laboratories) is used in all of the presented examples. It is preferred for its low price and low degree of unsaturation. Lecithin is also available from bovine heart. Soy bean lecithin is less expensive. It has a higher degree of unsaturation. Several synthetic varieties of lecithin are available which differ in chain length from 4 to 19 carbons (Supelco, Inc.). It is believed that lecithins with chain lengths in the biological range (10–18) are useful in various applications. Unsaturated lecithins (dioleoyl, dilinoleoyl; beta oleoyl; alpha-palmito beta oleoyl; alpha palmitoyl beta linoleoyl and alpha oleoyl beta palmitoyl) are also available. Diarachidonyl lecithin (highly unsaturated and a prostaglandin precursor) is also available.

Phosphatidic acid is available from egg or as synthetic compounds (dimyristoyl, dipalmitoyl or distearoyl, Calbiochem). Bovine phosphatidyl serine is available (Supelco or Calbiochem).

Phosphatidyl inositol is available from plant (Supelco) or bovine (Calbiochem) sources. Cardiolipin is available (Supelco) from bovine or bacterial sources. Phosphatidyl glycerol is available from bacterial (Supelco) cources or as synthetic compounds (dimyristoyl or dipalmitoyl; Calbiochem).

Phosphatidyl ethanolamine is available as egg, bacterial, bovine or plasmalogen (Supelco) or as synthetic compounds dioctadecanoyl and dioleoyl analogues and dihexadecyl, dilauryl, dimyristoyl and dipalmitoyl (Supelco and Calbiochem).

Monoglycerides are available from Sigma Chemcial Co. (1-monopalmitoyl-(rac)-glycerol, monopalmitin; 1-monocaprylol-(rac)-glycerol, monocaprylin; 1-monooleoyl-(rac)-glycerol(C18:1, cis-9), monoolein; 1-monostearyl-(rac)-glycerol, monostearin).

Other constituents:

It is possible to add other constituents to the microcrystal to increase its stability or modify its rate of release. For example, pharmacologically-acceptable oils can be added at low weight concentration to facilitate contact between the microcrystal and the phospholipid or glycerol lipid coating. It is necessary that the type of oil and its weight concentration be chosen such that the crystalline drug not be dissolved by the oil and that the coating by the membrane-forming lipid not be disrupted. These relationships can be determined empirically. Useful oils include, but are not limited to, vitamin E, isopropyl myristate, benzyl benzoate, oleyl alchohol, mineral oil, squalene and vegetable oil.

It is also possible to "precoat" the microcrystals by phospholipid-compatible, non-antigenic molecules which are solid at 37° C. Examples include paraffin, tristearin, ethyl oleate, cetostearyl alcohol, cetyl alcohol, myristyl alcohol, stearyl alcohol and petrolatum. For example, these materials can be incorporated into the primary coating by sonication or shear at temperatures above their melting points. Stabilization can be achieved by adding lecithin during the process as temperature is allowed to return to the solidification point of these material. It is desirable to use low weight concentrations ($\leq 10\%$) of such that the payload is not degraded, the rate of dissolution of the drug is not unduly impeded. Also, biodegradability may impose a further limitation.

Suspending medium:

In the final preparation, the continuous phase is generally water, buffered to a physiologically-acceptable pH and containing an iso-osmotic concentration of sodium chloride, glucose, mannitol or other osmotic agent. In certain applications involving intra-muscular injection of large volumes of microcrystals at high concentration, it is usefjul to increase the osmolarity of the medium (e.g. glucose concentration) to facilitate the spreading of the material in the muscle. As noted above, this can retard the process of compaction after intra-muscular injection. Where permissible, viscosity-increasing agents such as carboxycellulose can be useful to alter the pharmacokinetics following intra-muscular injection and to decrease the rate of sedimentation of the microcrystals upon storage.

In certain applications it is useful to substitute a polar solvent for water providing the bio-molecule's solubility in these is less than in water and that the solvents do not denature the bio-molecule. Examples of non-aqueous polar solvents which can be used include, but are not limited to the following: glycerin (water-miscible liquid with a dielectric constant of 42.5) and propylene glycol (water-miscible liquid with a dielectric constant of 32). The coated microcrystals can be made in these media, or can be allowed to sediment into these media. The primary requirement is that a substantial portion of the phospholipid or coating material be in membranous form in this solvent.

Preservatives

Oil-soluble preservatives can be added in process during the primary or coating phase. These include, but are not limited to, benzalkonium chloride, propylparabem, butylparaben, and chlorobutanol. There are also numerous water- and oil-soluble agents which can be added to the finished product as preservatives, including, benzyl alcohol, phenol, sodium benzoate, EDTA, etc.

Weights and measures

All parts and percentages reported herein are by weight (w/w) or weight/volume (w/v) percentage, in which the weight or volume in the denominator represents the total weight or volume of the system. Concentrations of water soluble constituents in aqueous solution (e.g. glucose) are given in millimolar concentration (mM=millimoles per liter) referred to the volume of water in the system. All temperatures are reported in degrees Celsius. Diameters or dimensions are given in millimeters (mm = $10^{-3}$ meters), micrometers (um = $10^{-6}$ meters), nanometers (nm = $10^{-9}$ meters) or Angstrom units (=0.1 nm). The compositions of the invention can comprise, consist essentially of or consist of the materials set forth and the process or method can comprise, consist essentially of or consist of the steps set forth with such materials.

DETAILED DESCRIPTION OF THE INVENTION

EXAMPLE 1

Heparin (0.3 gm) is precipitated from aqueous solution by addition of 0.3 gm protamine. The insoluble material is washed, resuspended in 3.0 ml isotonic glucose, 0.6 ml egg lecithin are added and the mixture is sonicated for 20 min to produce lecithin-coated microcrystals (solid microparticles) of protamine-heparin complex.

EXAMPLE 2

Tristearin (0.6) and 0.3 gm egg lecithin is added to 3.0 ml of isotonic glucose containing bovine serum albumin (BSA) at 5 mg/ml. The mixture is sonicated for 10 min, 0.3 gm egg lecithin are added, and the mixture is homogenized with a Polytron ® apparatus to yield lecithin-coated tristearin microcrystals (solid microparticles) entrapping 0.5% BSA in water-soluble form.

EXAMPLE 3

The preparation of Example 3 in which the water-soluble antibiotic gentamycin is substituted for BSA. This product constitutes lecithin-coated tristearin microcrystals (solid microparticles) entrapping 0.5% gentamycin in water-soluble form.

EXAMPLE 4

The preparation of Example 1 in which both the protamine-heparin precipitation and the sonication were carried out in the presence of a 1% suspension of 10 nm diameter colloidal iron oxide ($Fe_3O_4$) particles in buffered isotonic glucose solution. This constitutes magnetically manipulatable lecithin-coated microcrystals (solid microparticles) of protamine-heparin complex.

EXAMPLE 5

One gm of erythromycin and 1 gm egg lecithin are added to 3 ml of a 1% suspension of 10 nm diameter colloidal iron oxide ($Fe_3O_4$) particles in buffered isotonic glucose solution and the mixture is sonicated for 20 min. This constitutes magnetically manipulatable lecithin-coated microcrystals of the water-insoluble drug erythromycin.

EXAMPLE 6

Egg lecithin (Pfanstiehl, P-123, Pfanstiehl Laboratories, Waukegan, Ill.) is added to a lightly-buffered isotonic glucose solution to a final concentration of 20% (w/v) and is dispersed at high speed with a Polytron ® apparatus. This results in a syringable dispersion consisting primarily of <3 um diameter structures as revealed by Coulter N4-MD Submicron Particle Analyzer and visualization under a light microscope. Experiments with entrapment and exclusion of membrane-impermeant dyes such as carboxyfluorescein show that greater than 50% of the system volume is enclosed within lipid membranes. If the preparation is "doped" with Nile Red as a fluorescent marker for the lipid membrane phase and visualized under fluoresence microscopy, the suspension appears homogeneous red at normal concentration, but individual liposomes can be resolved when the preparation is diluted. After sterilization with gamma irradiation (1.5 mega-rad) the structures can be shown to remain stable for many months.

EXAMPLE 7

To a 10% (w/v) aqueous solution of the water-soluble antibiotic gentamycin was added egg lecithin to a final concentration of 25% (w/v), and the mixture was homogenized for 10 min with a Polytron ® to yield gentamycin-containing multilamellar liposomes at high concentration. Intra-muscular injection into a dog gave slowed release relative to free gentamycin.

EXAMPLE 8

Vitamin E microdroplets were added to a pseudorabies vaccine to give a final concentration of 10% (w/v) vitamin E, 3% (w/v) egg lecithin and normal antigen concentration. The combination was tested in guinea pigs. Antiviral antibody titer and survival upon challenge with virulent pseudorabies virus were superior to a commercial product having identical antigen concentration.

What is claimed is:

1. A pharmaceutical delivery system for a water-soluble biological molecules consisting essentially of a syringable, injectable aqueous suspension of solid particles of the bio-molecule in a complexed water-insoluble form, the solid particles having diameters or maximal dimensions of about 0.05 um to about 10 um, coated with a 0.3 nm to 3.0 um thick layer of a membrane-forming amphipathic lipid which stabilizes the bio-molecules in complexed solid form against coalescence and renders the bio-molecule in solid form, which composition is substantially devoid of uncoated particles.

2. A pharmaceutical delivery system for a water-soluble biological molecules consisting essentially of a syringable, injectable aqueous suspension of solid particles of the bio-molecule in a complexed water-insoluble form, the solid particles having diameters or maximal dimensions of about 0.05 um to about 10 um, coated with a 0.3 nm to 3.0 um thick encapsulating primary layer consisting of coating and enveloping layers of a membrane-forming layer of first a membrane-forming amphipathic lipid which stabilizes the bio-molecules in complexed solid form against coalescence and renders the bio-molecules in complexed solid form, and 25 nm to 3.0 um thick secondary layer consisting of a second membrane-forming amphipathic lipid in vesicular form associated with and surrounding but not enveloping the lipid-encapsulated solid-form bio-molecules, which composition is substantially devoid of uncoated particles.

3. A pharmaceutical delivery system for water-soluble drugs or biological molecules consisting essentially of a syringable, injectable aqueous suspension of solid particles of a pharmacologically-acceptable water-insoluble substance, the solid particles having diameters or maximal dimensions of about 0.05 um to about 10 um, coated with a 0.3 nm to 3.0 um thick layer of a membrane-forming amphipathic lipid which stabilizes the solid particles of a pharmacologically-acceptable water-insoluble substance against coalescence, wherein the water-soluble drug or bio-molecules are entrapped within the layers of membrane-forming lipid.

4. A pharmaceutical delivery system for a water-soluble drug or biological molecules consisting essentially of a syringable, injectable aqueous suspension of solid particles of a pharmacologically-acceptable water-insoluble substance, the solid particles having diameters or maximal dimensions of about 0.05 um to about 10 um, coated with a 0.3 nm to 3.0 um thick encapsulating primary layer consisting of coating and enveloping layers of a membrane-forming amphipathic lipid which stabilizes the pharmacologically-acceptable substance in solid form against coalescence, wherein the water-soluble drug or bio-molecules are entrapped within the layers of membrane-forming lipid.

5. The compositions of claim 1, 2, 3 or 4 wherein the solid particles also contain magnetic iron oxide ($Fe_3O_4$) particles having diameters maximal dimension of about 5 nm to about 10 um.

6. A syringable, injectable pharmaceutical composition consisting essentially of an aqueous suspension of crystals or solid particles of a pharmacologically active water-insoluble drug substance in solid form, the solid particles having diameters or maximal dimensions of about 0.05 um to about 10 um, coated with a 0.3 nm to 3.0 um thick layer of a membrane-forming amphipathic lipid which stabilizes the drug substance from coalescence and renders the drug substance in solid form less irritating to living tissue, which composition contains colloidal iron oxide (Fe$_3$O$_4$) particles of about 5 nm to about 10 um diameters or maximal dimensions, which composition is substantially devoid of uncoated crystals or drug or iron oxide particles.

7. A syringable, injectable pharmaceutical composition consisting essentially of an aqueous suspension of solid particles of a pharmacologically active water-insoluble drug substance in solid form, the crystals or solid particles having diameters or maximal dimensions of about 0.05 um to about 10 um, coated with a 0.3 nm to 3.0 um thick encapsulating primary layer consisting of coating and enveloping layers of a membrane-forming amphipathic lipid, which stabilizes the drug substance from coalescence, and 25 nm to 3.0 um thick secondary layer consisting of a membrane-forming amphipathic lipid in vesicular form associated with and surrounding but not enveloping the lipid-encapsulated drug particles, which composition contains colloidal iron oxide (Fe$_3$O$_4$) particles of about 5 nm to about 10 um diameters or maximal dimensions, which composition is substantially devoid of uncoated crystals or drug or iron oxide particles.

8. A solid pharmaceutical composition consisting essentially of the compositions of claims 1, 2, 3 or 4, devoid of water which, when water is added, gives an aqueous suspension.

9. The compositions of claims 1, 2, 3 or 4, in which the crystals or particles are wetted with a water-immiscible oil of up to 0.25 gram per gram crystalline or solid substance, to facilitate contact between the solid substance and the primary of amphipathic membrane-forming lipid, or to slow the rate of dissolution of crystals or solid substance or to otherwise modify the rate of release of pharmacologically-active substance.

10. The composition of claim 1, 2, 3 or 4 in which the bio-molecule is an antigen.

11. The composition of claim 10 in which the antigen is a bacterial membrane or a viral coat fragment.

* * * * *